United States Patent [19]

Huprich

[11] Patent Number: 5,192,536
[45] Date of Patent: Mar. 9, 1993

[54] METHOD AND COMPOSITION FOR COATING A WOUND WITH POLYETHER POLYURETHANE

[76] Inventor: Carl A. Huprich, 22333 County Rd. 62 North, Robertsdale, Ala. 36567

[21] Appl. No.: 794,680

[22] Filed: Nov. 19, 1991

Related U.S. Application Data

[63] Continuation-in-part of Ser. No. 605,105, Oct. 26, 1990, abandoned.

[51] Int. Cl.⁵ .................. A61K 9/70; A61L 15/26; A61L 25/00; A61F 13/02
[52] U.S. Cl. ...................... 424/78.08; 424/78.37; 424/78.06; 424/78.07; 424/443; 424/445; 602/43; 602/54; 602/904; 604/304; 523/111; 428/423.4
[58] Field of Search .............. 424/78, 443, 445, 447, 424/78.06–78.07, 78.37; 523/111; 524/367, 378; 428/423.4

[56] References Cited

U.S. PATENT DOCUMENTS

| | | | |
|---|---|---|---|
| 4,156,067 | 5/1979 | Gould | 424/444 |
| 4,784,857 | 11/1988 | Berry et al. | 424/443 |
| 4,867,150 | 9/1989 | Gilbert | 428/286 |

Primary Examiner—Thurman K. Page
Assistant Examiner—E. J. Webman

[57] ABSTRACT

A composition and a method for coating a wound is described. The composition consists of a mixture of 20 parts by weight of polyether polyurethane resin pellets being dissolved in about 80 parts by weight of tetrahydrofuran thereafter mixing the solution in order to provide complete mixing in an air tight container. The composition then being applied to a wound to form a tough but elastic wound coating to promote healing of animal tissue.

7 Claims, No Drawings

METHOD AND COMPOSITION FOR COATING A WOUND WITH POLYETHER POLYURETHANE

This application is a continuation-in-part of application Ser. No. 605,105 filed Oct. 26, 1990 now abandoned.

BACKGROUND

This invention generally relates to a method and composition for coating the wound of an animal. More specifically it relates to a method of coating a wound with a liquid for the purpose of allowing the wound to heal itself; more particularly the liquid is applied to the wound, thereafter drying forming a membrane-like cover over the wound. Furthermore, a composition for the coating material is described.

Wound coatings and/or bandages have been described in the prior art. Sullivan, in U.S. Pat. No. 2,824,559, described a plastic cot or bandage for covering and protecting hands and other parts of the body, including, wounds. Firth, et al, in U.S. Pat. No. 3,682,179, described a method for treating and repairing wounds of animals by applying urethane resin to hoof surfaces. Dell, et al, in U.S. Pat. No. 4,584,192, described a film forming composition for protecting wounds and releasing anti-microbial agents to the skin. Webster, in U.S. Pat. No. 4,664,662, described an absorbent wound dressing suitable for use in deep and cavernous wounds. Horiuchi, et al, in U.S. Pat. No. 4,880,416, described a dermal bandage comprising a film-like adhesive material for protecting wounds. Gould, in U.S. Pat. No. 4,156,067, described a polyurethane polymer which could be used in drug delivery systems or as burn dressings.

However, as will be shown by way of explanation and drawings, the present invention works in a novel manner and differently from the prior inventions.

SUMMARY OF THE INVENTION

The present invention describes a method and composition for coating and treating a wound.

The composition comprises 80 parts by weight of a solvent, e.g., methyl ethyl ketone or tetrahydrofuran 20 parts by weight polyether polyurethane resin e.g. Estane, in the form of pellets, thereafter dissolving said pellets in the solvent by way of high speed agitation in vapor type containers. It should be noted that complete dissolution of the pellets may require setting for a period of 8 to 12 hours.

The composition described above is thereafter used as part of a method of coating a wound. The composition is applied in the form of a liquid after dissolution occurs as previously discussed. Said liquid coating is applied directly to a wound by brushing or pouring over the wound. The coating dries rapidly into a waterproof, windproof non-perforated nonfibrous elastic, and adherent film that breathes somewhat like skin. The dried film is suitable for covering, protecting and holding in place medicated or unmedicated paper covering the wound.

Some of the objectives and advantages of the present invention are as follows: the film is tough but elastic; the film is permeable to vapors, i.e., it breathes like human-like skin; the film is waterproof, wind and air proof since it has no perforations; it prevents contamination by dirt. Furthermore, it prevents insect irritation or biting; the film adheres to dry skin but growing skin does not stick to it, it is non-toxic and non-carcinogenic; it promotes and enhances healing by protecting the wound and/or covered area; it assists in maintaining closure of the wound; it is aerobic bacteriostatic; and it may be peeled from the skin. Another advantage is that it can be applied to multiply curved surfaces, e.g., one's knuckles, and maintain an airtight seal and that it forms itself to the particular shape as it dries.

DESCRIPTION OF THE PREFERRED EMBODIMENT

The present invention describes a composition for and a method of coating a wound. The composition is formed by dissolving about 20 parts by weight of Estane pellets, which is a polyether polyurethane resin, in about 80 parts of a solvent such as tetrahydrofuran. It is believed that similar solvents such as methy ethyl ketone may also be used. Dissolution of the pellets in the solvents is assured by means of high speed agitation in a vapor tight container, e.g., a Cowles mixer. Complete dissolution may require the composition to remain overnight, for example, 8 to 12 hours.

The solution made as described above is a syrupy like liquid suitable for pouring or spreading. The viscosity of the liquid can be modified by varying the amounts of the solvent. Applicant's research of the films resulting from the present invention indicates that the Moisture Vapor Transmission Rate would range from about 76.0 to about 128.0 gm/100 sq.in/24 hrs. per mil of thickness.

The present invention also describes the method of directly coating a wound. The composition previously described is applied by brushing or pouring over a wound of a mammal. The mammals could be an animal such as farm animals and possibly humans. The coating dries rapidly into a waterproof, windproof, elastic, and adherent film that allows the passage of air, i.e., it breathes somewhat like live skin.

The syrupy solution dries quickly by evaporation on the skin of the patient animal. The dried film is suitable for covering, protecting and holding in place medicated or unmedicated material, e.g. paper, covering the wound The tetrahydrofuran is a defatting agent, but the short exposure time has no apparent effect on the skin. In fact, in the development of this material and its application to our animals e.g. horses, neither the animals nor the people applying the wound coating have had any skin problems. The wound coating bonds to the skin but can be readily removed by peeling similar to the removal of an adhesive bandage. The coating is not intended for food producing or milk producing animals. The wound coating has been successfully tested on horses.

What is claimed is:

1. A method for coating a wound comprising the steps of:
   (a) coating a wound with a mixture consisting of polyether polyurethane resin and tetrahydrofuran
   (b) allowing said mixture to dry thereafter forming a nonfibrous film whereby healing is promoted.

2. The method of claim 1 further comprising coating a wound with a mixture comprising about 20 parts by weight of polyether polyurethane resin and about 80 parts by weight tetrahydrofuran.

3. The method of claim 2 wherein said coating is waterproof.

4. The method of claim 2 wherein said coating is porous to air.

5. The method of claim 2 wherein said coating is aerobic bacteriostatic.

6. The method of claim 2 wherein said coating is elastic.

7. The method of claim 2 wherein said coating is applied directly to the wound.

* * * * *